United States Patent [19]
Kubota et al.

[11] Patent Number: 5,679,575
[45] Date of Patent: Oct. 21, 1997

[54] PARTICLE MEASURING APPARATUS AND METHOD

[75] Inventors: Fumio Kubota, Nishinomiya; Keiichi Inami, Kobe, both of Japan

[73] Assignee: TOA Medical Electronics, Co., Ltd., Hyogo, Japan

[21] Appl. No.: 575,960

[22] Filed: Dec. 21, 1995

[30] Foreign Application Priority Data

Dec. 21, 1994 [JP] Japan .................. 6-318467

[51] Int. Cl.$^6$ .................................................. G01N 35/08
[52] U.S. Cl. .................. 436/49; 436/54; 436/179; 436/180; 422/63
[58] Field of Search .............. 422/68.1, 63; 436/49, 436/54, 179, 180

[56] References Cited

U.S. PATENT DOCUMENTS

| | | | |
|---|---|---|---|
| 5,079,959 | 1/1992 | Miyake et al. | 73/864.85 |
| 5,130,095 | 7/1992 | Ricchio et al. | 422/63 |
| 5,132,233 | 7/1992 | Jackson et al. | 436/179 |
| 5,256,573 | 10/1993 | Kuroda et al. | 436/179 |

FOREIGN PATENT DOCUMENTS

| | | |
|---|---|---|
| 280937 | 3/1990 | Japan. |
| 631148 | 2/1994 | Japan. |

*Primary Examiner*—Jeffrey Snay
*Attorney, Agent, or Firm*—Birch, Stewart, Kolasch, & Birch, LLP

[57] ABSTRACT

The particle measuring apparatus includes a specimen pipetting section for pipetting a specimen liquid, a reagent dispensing section for dispensing a reagent, a mixing section for receiving the specimen liquid supplied by the specimen pipetting section and the reagent dispensed by the reagent dispensing section and a flow cell for receiving the specimen liquid and the reagent transferred from the mixing section and measuring particles therein; the pipet being so constructed as to be positioned in a first state of picking up the specimen liquid as well as in a second state of supplying the specimen liquid into the mixing section, the mixing section being open when the pipet is in the first state, the mixing section being kept closed by the pipet in the second state so that the reagent dispensed by the reagent dispensing section can press and transfer the specimen liquid in the mixing section out toward the particle measuring section.

20 Claims, 8 Drawing Sheets

Conventional Method for Dispensation into A Chamber Using A Pipet

Conventional Method for Dispensation Using the Difference in Sucked Amounts

Conventional Method for Dispensation Using A Sampling Valve

PARTICLE MEASURING APPARATUS AND METHOD

BACKGROUND OF THE INVENTION

1. Field of the Invention

The present invention relates to a particle measuring apparatus, particularly provided with specimen supplies including a pipet, a syringe and the like, a reagent dispenser, a mixing section for receiving a specimen liquid from the specimen supplying means and a reagent from the reagent dispensing means, and a particle measuring section for measuring particles in the specimen liquid. More particularly, the present invention relates to improvements in diluting and mixing of the specimen liquid and cleaning of liquid passageways in a particle measuring apparatus for counting blood cells in the specimen liquid such as a little amount of blood by diluting the specimen liquid with a reagent and leading the diluted specimen liquid into a flow cell.

2. Description of the Related Art

A quantitative dispensing system by pipetting as shown in FIG. 12 is known as one of dispensing systems for supplying a predetermined amount of specimen liquid and reagent in conventional apparatuses for measuring particles such as blood cells. The system is provided with an open mixing container 101 for mixing a specimen liquid and a reagent, a pipet 104 connected with a syringe 102, and a reagent supply mechanism including a reagent container 105 and a syringe 106. The pipet 104 is structured so as to be movable between a specimen pipetting position where a specimen 103 is disposed and a specimen discharge position above the open mixing container 101. The specimen discharged from the pipet 104 and the reagent discharged from the syringe 106, after being mixed in the open mixing container 101, are led to a flow cell, and then particles in the diluted specimen liquid are optically measured. Liquid passageways are cleaned with washings supplied into the open mixing container 101 by the syringe 102 or 106.

Another dispensing system is shown in FIG. 13, wherein a pipet 111, a syringe 112 communicated with a reagent container 105, and a syringe 114 are connected in parallel by a pipeline 115. The syringe 112 serves to discharge a reagent into the pipeline 115 at a flow rate Q2, and then the syringe 114 sucks the liquid from the pipeline at a flow rate Q1. Thus at a difference between the flow rates, namely at a flow rate of Q1–Q2, the pipet 111 sucks a specimen, which is mixed with the reagent 105 in the pipeline 115.

Still another quantitative dispensing system as shown in FIG. 14 is practiced wherein a sampling valve is used. In the system, a predetermined amount of specimen 103 is led into a sampling valve 123 from a piper 122 by means of a drive of a suction pump 126, and then a predetermined amount of reagent is discharged into the sampling valve 123 by a syringe 121. These liquids discharged into the sampling valve 123 are then sent into a mixing container 124. The obtained diluted specimen liquid is transferred to a flow cell. The sampling valve 123 usually serves to perform a predetermined-fold dilution by extruding the specimen fulling in a cylindrical dispensing passageway provided as a moving element therein, with a predetermined amount of dilution agent.

In the pipet dispensing shown in FIG. 12, a desired mixture can be obtained with stirring in the mixing container 101 when the amount of specimen and reagent discharged and contained in the mixing container is within a suitable range. But when the amount of specimen used or the dilution is varied in a wider range, especially when the amount of specimen or reagent is extremely small, the satisfactory stirring cannot be performed in the mixing container 101. Further, when a large amount of reagent is required, the mixture may overflow the mixing container 101 since the container 101 is not closed. Probably different sizes of containers can be used according to the desired amount of the liquids, but the operation becomes complicated. That is, the system cannot meet various requirements in the measured amount of liquid.

Further in the above system, an additional means is required for transferring the mixture in the mixing container 101 to the flow cell.

Further in the above system, the specimen is likely to be contaminated by another specimen due to a poor cleaning of the mixing container 101, which adversely affects the accuracy of the measurement. In order to avoid this contamination, it is necessary to use a disposable mixing container or to clean the mixing container every time with a large quantity of washings. Particularly when a small amount of specimen is dispensed, a smaller mixing container certainly is more suitable for preventing the contamination, but a small container hinders efficient mixing and also cannot accept the increased amount of liquid measured.

In the dispensing system using a difference between the flow rates shown in FIG. 13, the specimen liquid remaining in a portion of the pipeline 115 between the pipet 111 and the syringe 114 is wasted when the mixture liquid is transferred to the flow cell. Moreover an additional means for cleaning the pipeline 115 must be provided in order to avoid contamination of different specimens. Further, when various kinds of specimens are successively measured, because the pipeline 115 is made up of a series of closed liquid passageways, the cleaning for the pipeline 115 is complicated, and the consequent repeated cleaning of the passageways needs a large amount of washings.

In the system using the sampling valve 123 shown in FIG. 14, for the purpose of changing the amount of specimen liquid and reagent to be dispersed, a plurality of dispensing passageways different in size and length must be formed in the moving device in the valve 123. Therefore, there is a limit to the range for setting the dispensed amount, and it is difficult to meet various requirements in the dispensed amount.

SUMMARY OF THE INVENTION

The present invention has been conceived in view of the above mentioned problems, and an object of the present invention is to provide a particle measuring apparatus which is intended to have a simple structure, allows an easy alteration in the dilution of specimen liquid and a reduction in the amount of specimen liquid, reagent or washings used and is capable of swifter and more accurate measurement.

The invention provides a particle measuring apparatus comprising a specimen pipetting section for pipetting a specimen liquid, a reagent dispenser for dispensing a reagent, a mixing section for receiving the specimen liquid supplied by the specimen pipetting means and the reagent dispensed by the reagent dispensing means, and a particle measuring section for receiving the specimen liquid and the reagent transferred from the mixing section and measuring particles therein, wherein the specimen pipetting section is so constructed as to be positioned in a first state of picking up the specimen liquid as well as in a second state of supplying the specimen liquid into the mixing section, the mixing section is open when the specimen pipetting section is in the first state, and the mixing section is kept closed by the specimen pipetting section in the second state, so that the reagent dispensed by the reagent dispensing means presses and transfers the specimen liquid in the mixing section out toward the particle measuring section.

Other objects, features and advantages of the invention will be apparent from the following description taken in connection with the accompanying drawing.

DESCRIPTION OF THE PREFERRED EMBODIMENTS

Figure 1:
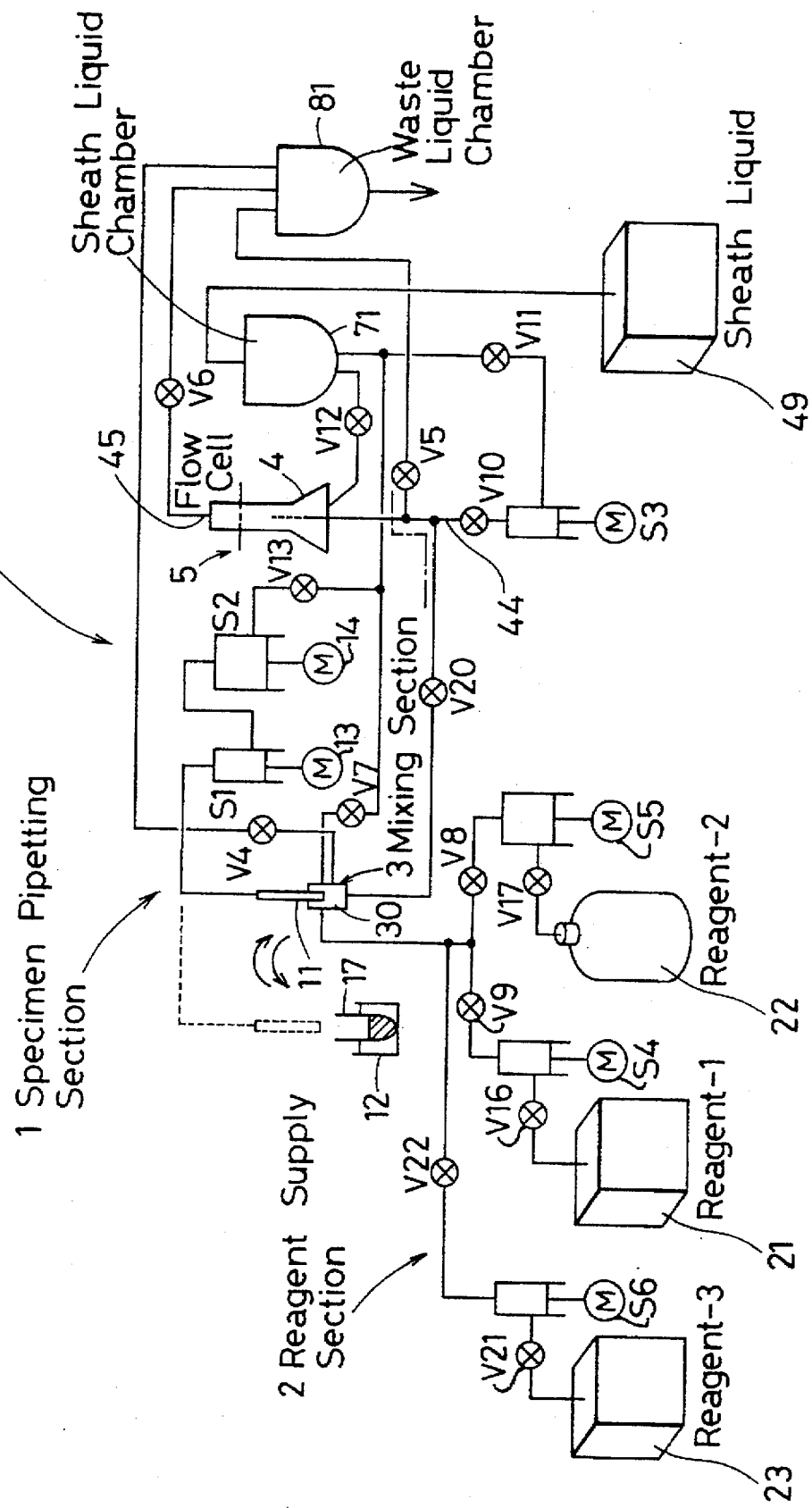
FIG. 1 is a schematic view of a particle measuring apparatus embodying the present invention.

The specimen pipetting section of the invention may be specifically provided with a pipet whose tip can be inserted into a specimen container, and a pipet moving mechanism which, supporting a base of the pipet, is capable of moving the tip of the pipet vertically as well as horizontally, picking up by suction the specimen liquid from the specimen container and discharging the specimen liquid into the mixing section.

The reagent according to the invention is in the form of solution and at least capable of dissolving or dispersing the specimen liquid.

The reagent dispenser of the invention may specifically be connected to the mixing section by a passageway and serve to transfer by pressure the reagent into the mixing section by means of a drive of a pump, a syringe or the like.

"To mix" according to the invention means to put the specimen liquid and the reagent together for leading them in either a homogeneous or heterogeneous state into the passageway, where the specimen liquid is dissolved or dispersed by the reagent before the specimen liquid is received by the particle measuring section.

The mixing section of the invention is preferably a container with at least one opening for receiving the specimen liquid and/or the reagent, provided with passageways for receiving washings and for discharging the waste thereof.

Preferably the specimen pipetting section has a tube-like pipet, the mixing section has a container with an opening for receiving the specimen liquid, and the mixing section is kept closed by contacting the periphery of the pipet with the opening.

"To keep the mixing section closed" according to the invention means to keep the mixing section closed to such an extent that the reagent dispensed by the reagent dispensing section can press and transfer the specimen liquid in the mixing section toward the particle measuring section and the liquid in the mixing section does not leak out from the opening.

The periphery of the pipet and the opening of the container preferably contact each other with a seal member therebetween.

The seal mechanism of the invention, though not particularly limited, may be by an elastic member such as a packing or by fitting.

The particle measuring section of the invention, though not particularly limited, may be by a sheath flow method, for example.

The specimen liquid according to the invention, though not specifically limited, may be blood containing blood cells. The reagent may be a dyeing agent, a hemolysing agent or other agent. For example, when reticulocytes are first measured and then leukocytes are measured by use of a reagent 1: a buffer, a reagent 2: a dyeing liquid (auramin O, etc.), a reagent 3: a hemolysing agent (NONIPOL(trade name), etc.), a whole blood specimen as a specimen liquid is mixed with the reagents 1 and 2 for the measurement of reticulocytes, and with the reagents 2 and 3 for the measurement of leukocytes. The dilution of the specimen for the measurement of reticulocytes is usually around 200 times. The amount of specimen actually used for the measurement is usually as small as about 10 µl (at a discharge rate of 2.5 µl/sec.; for a discharge time period of four seconds). The dilution of the specimen for the measurement of leukocytes is usually around four times. The amount of specimen actually used for the measurement is usually about 220 µl (at a discharge rate 55 µl/sec.; for a discharge time period of 4 seconds).

In the particle measurement of the invention, steps are not particularly limited. To take an example using the above mentioned blood specimen for illustration, 230 µl of blood is pipetted by the specimen pipetting section, 10 µl out of which is supplied into the mixing section (at a discharge rate of 2.5 µl/sec.; for a discharge time period of 4 seconds). At the same time, in order to dilute 200 times the specimen, 40 µl of the reagent 2 and 1,950 µl of the reagent 1 are supplied into the mixing section by the reagent dispensing means (for the reagent 1 at a discharge rate of 10 µl/sec. and for the reagent 2 at a discharge rate of 487.5 µl/sec., both for a discharge time period of four seconds). Then the mixture (the specimen liquid, the reagent 1 and the reagent 2) is transferred to the particle measuring section provided with the flow cell, and a desired measurement of the erythrocytes is performed. Following the measurement of the erythrocytes, the rest of the blood, 220 µl, is supplied into the mixing section (at a discharge rate of 55 µl/sec.; for a discharge time period of four seconds). At the same time, in order to dilute 4 times the specimen liquid, 17.6 µl of the reagent 2 and 642.4 µl of the reagent 3 are supplied into the mixing section by the reagent dispensing means (for the reagent 2 at a discharge rate of 4.4 µl/sec. and for the reagent 3 at a discharge rate of 160.6 µl/sec., both for a discharge time period of four seconds). Then the specimen liquid and reagent are also transferred to the particle measuring section and a desired measurement of the leukocytes is performed.

Preferably, in the mixing section or in the passageway communicating the mixing section with the particle measuring section, a turbulence generator is provided for generating a turbulent flow in the specimen liquid and reagent transferred therein.

The turbulence generator is preferably made of a member projecting into the mixing section or into the passageway communicating the mixing section with the particle measuring section.

Preferably the mixing section is provided with a passageway for receiving washings, the passageway communicating the mixing section with the particle measuring section is provided with a branch passageway for discharging a waste liquid, and the projecting member is a rod-like member inserted through the branch passageway whose tip projects into the communicating passageway.

The particle measuring apparatus of the invention preferably has a plurality of reagent dispensers provided with their respective passageways which join together to communicate with the mixing section.

The particle measuring apparatus of the invention preferably has a plurality of reagent dispensers each of which is provided with a passageway independently communicating with the mixing section.

The particle measuring apparatus of the invention is preferably provided with setting mechanism for variably setting the dilution of the specimen liquid with the reagent.

The setting mechanism of the invention may contain a control section for controlling the reagent dispensing means, for example, controlling the syringe drive source which drives the syringe to such or discharge for a desired time.

In the particle measuring apparatus of the invention, the specimen pipetting section first pipets the specimen liquid in the first state, when the mixing section is open, and then moves in order to discharge the specimen into the mixing section, to the second state in which the specimen pipetting section contacts with the mixing section to keep it closed. Then the reagent is also supplied into the mixing section by the reagent dispenser. At this time, because the specimen pipetting section positioned in the second state keeps the mixing section closed, the reagent dispensed by the reagent dispensing means can press and transfer the specimen liquid in the mixing section toward the particle measuring section.

The above structure allows the specimen pipetting section to move repeatedly between the first state and the second state for pipetting any desired amount of the specimen liquid and also serves for an effective mixing of the specimen liquid and the reagent whatever the amount of the specimen liquid is.

Also the dilution with the reagent is widely changed only by controlling the discharge rate of the reagent dispensing means.

Further the possible reduction of the size of the mixing section saves the amount of washings for cleaning thoroughly the inside of the mixing section.

When the mixing section is so constructed as to be kept closed by the contact of the opening thereof for receiving the liquid with the periphery of the tube-like pipet of the specimen pipetting section, the mixing section can be kept closed better.

Further, when the contact of the opening of the mixing section with periphery of the pipet is with a seal member therebetween, more secured closure is obtained.

The specimen liquid and reagent can be better mixed by the turbulent flow when the turbulence generator is provided in the mixing section or in the passageway communicating the mixing section with the particle measuring section.

Then the turbulence generator is constituted of the member projecting either into the mixing section or into the passageway communicating the mixing section with the particle measuring section, the turbulence can be easily and effectively obtained.

Further, when the turbulence generator is constituted of the rod-like projecting member inserted into the branch passageway for discharging the waste liquid mounted to the passageway communicating the mixing section with the particle measuring section, the rod-like projecting member can be easily attached, detached or replaced.

When the particle measuring apparatus has such a construction to have a plurality of reagent dispensers provided with their respective passageways which join together to communicate with the mixing section, a portion of the passageway connecting all the reagent dispensing means with the mixing section can be omitted.

When the particle measuring apparatus has such a construction to have a plurality of reagent dispensers, each of which is provided with a passageway independently communicating with the mixing section, any undesirable reaction can be prohibited if the reagents react each other.

When the particle measuring apparatus is provided with the setting mechanism for variably setting the dilution of the specimen liquid with the reagent, the dilution can be easily and promptly changed.

In the following examples are described several preferred embodiments to illustrate the invention. However it is to be understood that the invention is not intended to be limited to the specific embodiments.

FIG. 1 is a view explaining a particle measuring apparatus 10 in one embodiment of the present invention. In this embodiment, the measurement of red and leukocytes in blood is explained using the particle measuring apparatus 10, but an object of the measuring apparatus 10 is not limited thereto. The apparatus 10 is constituted mainly of a specimen pipetting section 1, a reagent supply section 2 as the reagent dispenser, a mixing section 3, and a particle measuring section 5 including a flow cell 4 connected to the mixing section 3.

Figure 3:
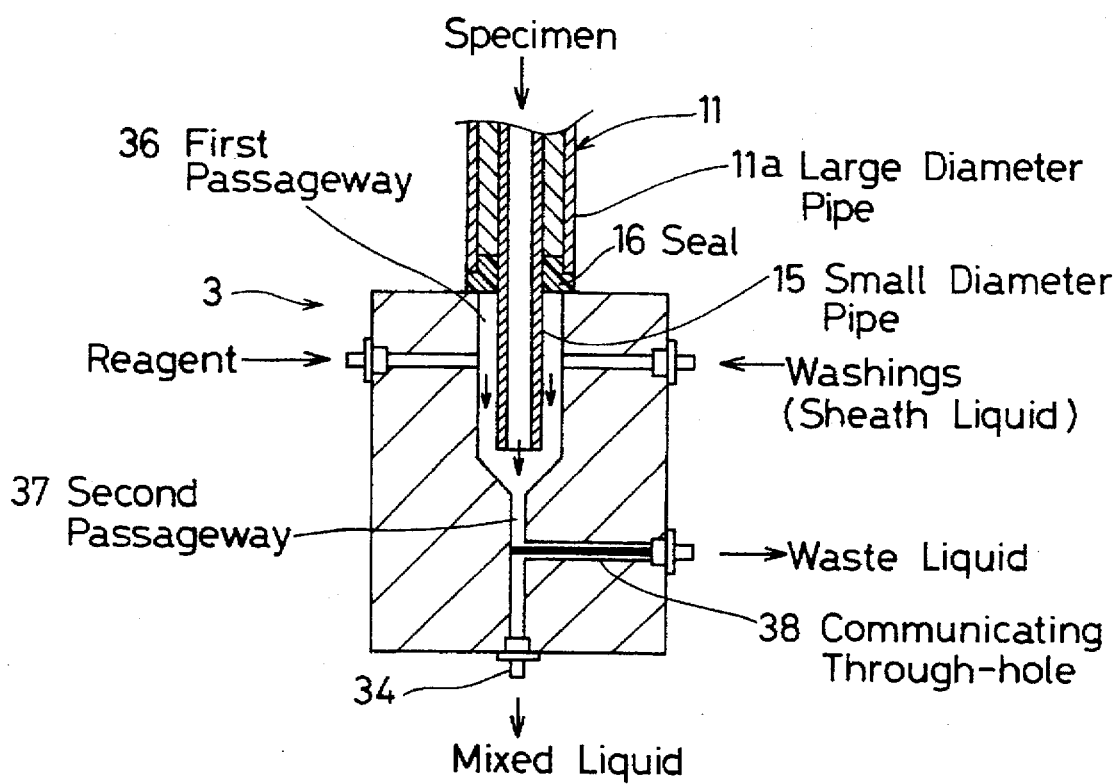
FIG. 3 is a cross sectional view of a mixing section illustrating a state wherein a tip of a pipet is inserted therein.

In the specimen pipetting section 1, a pipet 11, a syringe S1 for dispensing a small amount (10 to 100 µl), and a syringe S2 for dispensing a larger amount (100 to 1000 µl) are disposed in line. The syringes S1 and S2, provided with driving sources 13 and 14 respectively for driving pistons, are switched so as to be used according to a predetermined dilution. The pipet 11, as shown in FIG. 3, includes a large diameter pipe 11a and a small diameter pipe 15 extending downwardly from the large diameter pipe 11a, both the pipes being concentrically disposed. A seal member 16 is provided between the bottom end of the large diameter pipe 11a and the outer circumferential surface of the small diameter pipe 15. For example, the external diameter of the large diameter pipe 11a is 5 mm and that of the small diameter pipe 15 is 2 mm. To the upper part of the large diameter pipe 11a is mounted a three-dimensional moving mechanism, not shown, which moves the large diameter pipe 11a of the pipet between the initial position (the first state) above a specimen rack 12 and the specimen discharge position (the second state) wherein the small diameter pipe 15 of the pipet is inserted in the mixing section 3. The above structure enables the specimen pipetting section to suck in the initial position a blood specimen in a specimen container 17 placed on the specimen rack 12 and then to move to the specimen discharging position to discharge the blood specimen into the mixing section 3.

The reagent supply section 2 is constituted mainly of containers 21 to 23 for containing reagent 1 to 3, valves V16, V17 and V21 connected to the containers 21 to 23, and syringes S4, S5 and S6. In this embodiment, the reagent 1 is a buffer, the reagent 2 auramin O (a liquid for dyeing a nucleic acid), and the reagent 3 a hemolysing agent (a surfactant such as NONIPOL). The syringes S4, S5 and S6 are connected to the mixing section 3 via valves V9, V8 and V22, serving as dilution determining means.

Figure 2:
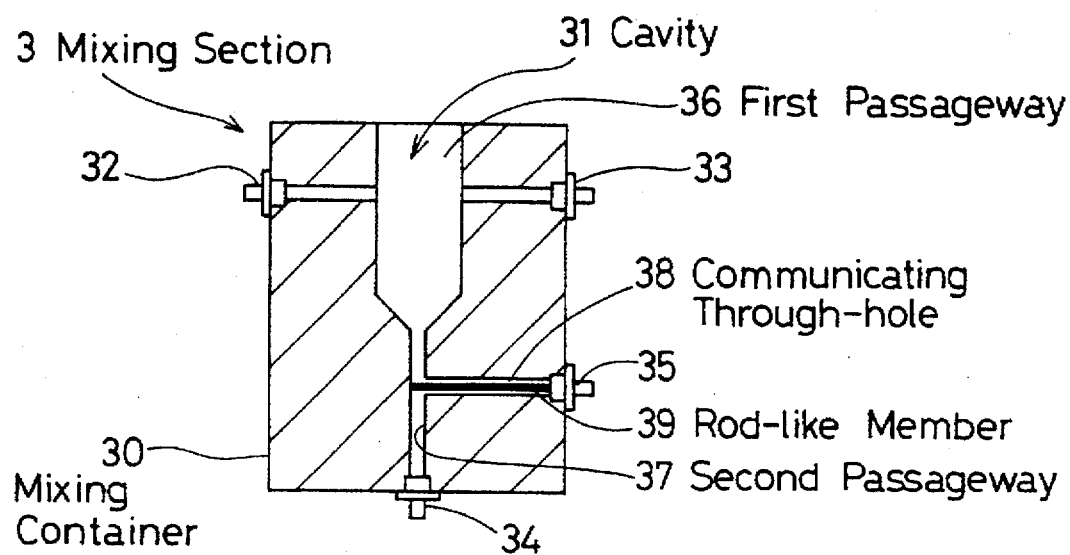
FIG. 2 is a cross sectional view of a mixing section in FIG. 1.

The mixing section 3, as shown in FIG. 2, is constituted mainly of a cavity 31 which has openings at the top and the bottom, and ports 32 to 35 which communicate with the cavity 31. The cavity 31 consists of a first passageway 36 with a large diameter formed in the upper part of the figure and a second passageway 37 with a small diameter formed under the first passageway 36. The diameter of the first passageway 36 is 2.6 mm and that of the second 37 is 1.00 mm. The first passageway 36 has such a bore as to allow the small diameter pipe 15 of the pipet 11 to be inserted. The ports 32 and 33 communicate with the first passageway 36, the port 32 connected to the reagent supply section 2, the port 33 connected to a later-described chamber 71 for sheath liquid via a valve V7. The port 34 is connected to an entrance of the flow cell 4 via a valve V20 disposed below the second passage way 37. The port 35 is communicated to the second passageway 37, making approximately right angles therewith, and connected to a chamber 81 for waste liquid via a valve four.

A rod-like projecting member 39 is inserted into a through-hole 38 communicating the second passageway 37 with the port 35 as a turbulence generator. The diameter of the communicating through-hole 38 is 1.00 mm and that of the rod-like member 39 is 0.7 mm, and therefore the attachment or detachment thereof is easy. One end of the rod-like projecting member 39 extends into the second passageway 37. A temperature control unit including a heater may be provided in the mixing section 3. In addition, FIG. 2 illustrates the initial position (the first state) of the pipet 11, namely the pipet 11 does not contact the mixing section 3. FIG. 3 illustrates the specimen liquid discharging state (the second state), namely the small diameter pipe 15 of the pipet is inserted into the mixing section 3.

The seal member 16 is an annular packing disposed between the bottom part of the large diameter pipe 11a and the small diameter pipe 15 of the pipet. When the small diameter pipe 15 descends into the first passageway 36 of the mixing section 3 by means of the pipet moving mechanism, the seal member 16, between the bottom part of the large diameter pipe 11a and the periphery of the upper opening of the cavity 31, serves to seal the cavity 31, acting as a seal mechanism.

Figure 4:
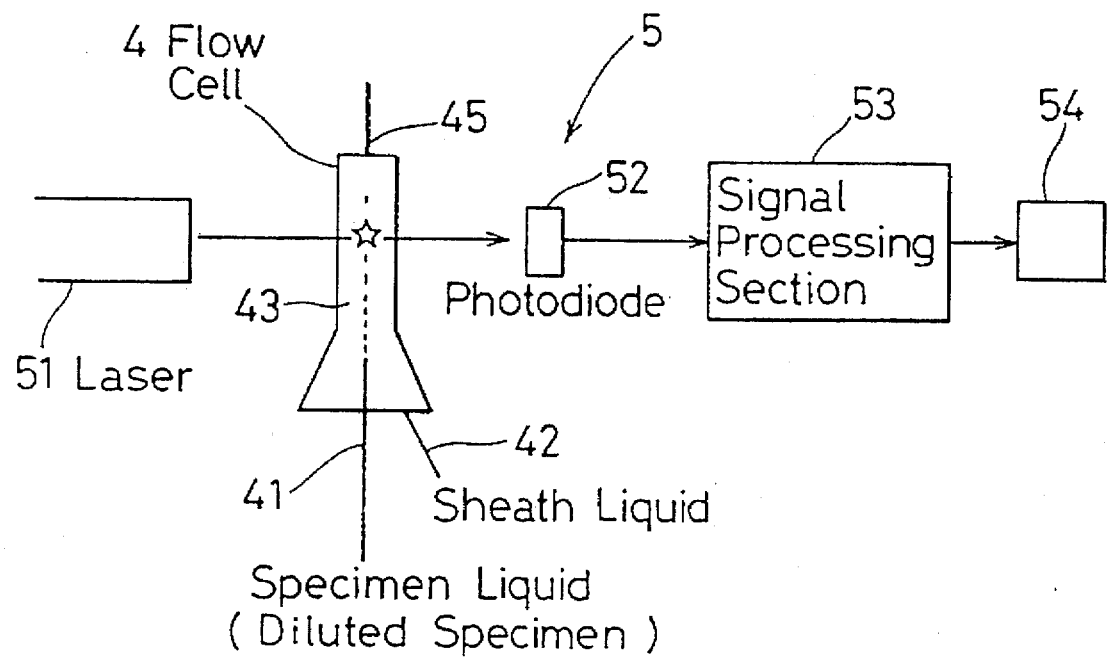
FIG. 4 is a schematic view of a measuring section according to FIG. 1.

The flow cell 4, as shown in FIG. 4, is made up of a light transmissible rectangular parallelopiped block, and includes a pipe 43 having a rectangular sectional shape on the longitudinal axis. The pipe 43 has an inner cross section of 0.3 mm×0.3 mm. Outside of the flow cell 4 is disposed a light source 51 (such as a laser) and a light detector 52 (such as a photodiode or photomultiplier) for detecting light from particles (such as forward scattered light or side fluorescence). A signal processing section 53 and CRT 54 are connected to the light detector 52.

At one end of the pipe 43 are disposed a nozzle 41 for discharging into the flow cell the diluted specimen made in the mixing section 3 and a sheath liquid inlet 42 for discharging a sheath liquid. The nozzle 41 is connected to a syringe S3 via a valve 10 by means of a pipeline 44. To the pipeline 44, a pipeline from the port 34 of the mixing section 3 is connected via the valve V20 as well as a pipeline from the waste liquid chamber 81 is connected via a valve V5. To the sheath liquid inlet 42, a pipeline from an outlet of the sheath liquid chamber 71 is connected via a valve 12. The outlet of the sheath liquid chamber 71 is connected to the syringe S3 via a valve V11. An entrance of the sheath liquid chamber 71 is connected to a sheath liquid tank 49.

The flow cell 4 has at the other end thereof a discharge outlet 45 for discharging the liquids supplied into the flow cell 4. The discharge outlet 45 is connected to the waste liquid chamber 81 via a valve 6.

Figure 5:
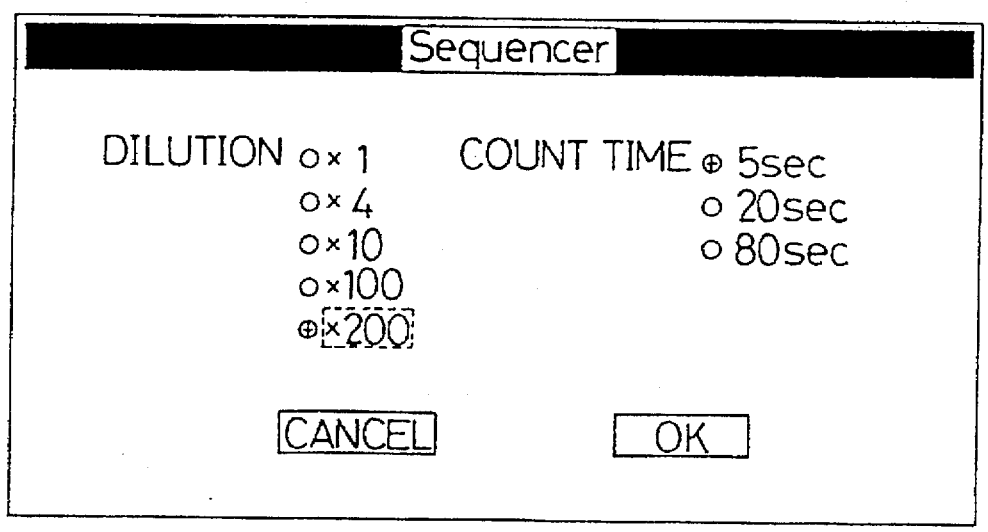
FIG. 5 illustrates an example for a setting screen of a display section connected to the measuring section in FIG. 4.

FIG. 5 is a display screen for an initial setting displayed in CRT 54. The display screen herein is set up so as to display multi stages of dilutions of the specimen and count times, that is, count times for counting particles like blood cells contained in the specimen which is flowing in the flow cell 4. The dilution is optionally selected from a predetermined program. The settings of the program can be fittingly changed. The count time is also optionally selected from the program. The dilution and count time are determined by operating a keyboard, not shown.

Table 1 explains a program for the dilutions of the specimen liquid set by operations on the screen and necessary amount of the liquid and the reagents for each dilution:

TABLE 1

| Dilution | Specimen (µl) | Reagent 1 (µl) | Reagent 2 (µl) | Suction amount by pipet (µl) |
|---|---|---|---|---|
| 1 | 900 | 0 | 0 | 930 |
| 4 | 220 | 17.6 | 642.4 | 250 |
| 10 | 90 | 18 | 792 | 110 |
| 100 | 15 | 30 | 1455 | 30 |
| 200 | 10 | 40 | 1950 | 15 |

Table 2 explains a program for the count times set by operations on the screen, the amount of the specimen and the required time for measurement:

TABLE 2

| Count time (seconds) | Analyzed amount (µl) | Amount of specimen at 200-fold dilution (µl) | Required time for measurement (seconds) |
|---|---|---|---|
| 5 | 0.93 | 0.005 | 65 |
| 20 | 3.71 | 0.019 | 80 |
| 80 | 14.86 | 0.074 | 150 |

The required time for measurement in the table means a total of the time for the suction of the specimen, that for the dilution mixing in the mixing section 3 (reaction time), the above-mentioned specimen count time and the time for the cleaning. The reaction time herein is 10 seconds.

Figure 6:
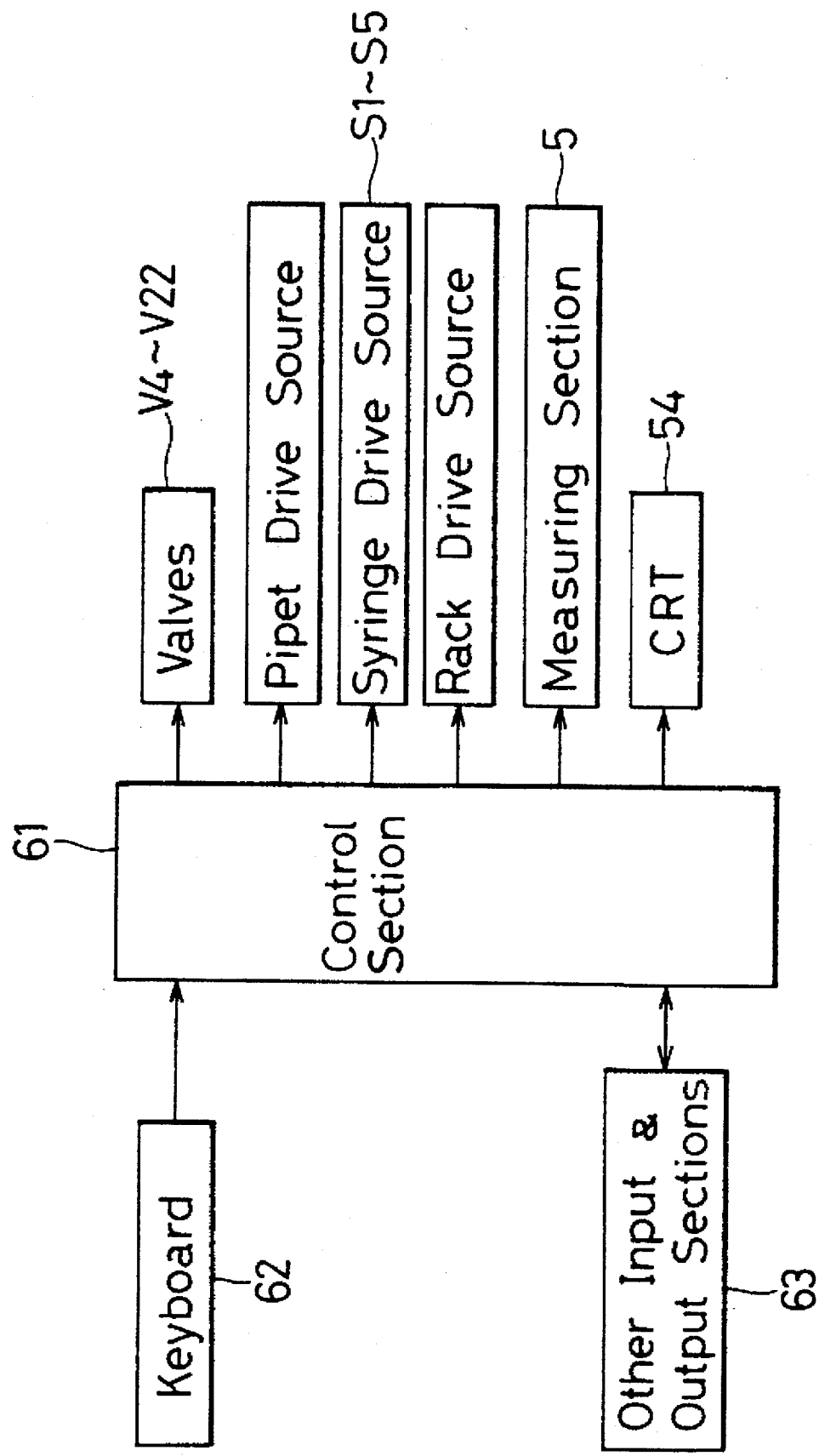
FIG. 6 is a block diagram illustrating a control section of a particle measuring apparatus according to the present invention.

FIG. 6 is a block diagram illustrating the particle measuring apparatus 10, which has a control section 61 including a microcomputer with CPU, ROM, RAM, a timer, a counter and the like. A keyboard is connected to the control section 61. Also each of the valves V4 to V13, V16, V17, V21, V22 and input and output sections of the respective drive sources of the pipet 11, the syringes S1 to S6 and the specimen rack 12 as well as an input and output sections of the measuring section 5, CRT 54 and other input and output sections 63 are connected to the control section 61.

Figure 7:
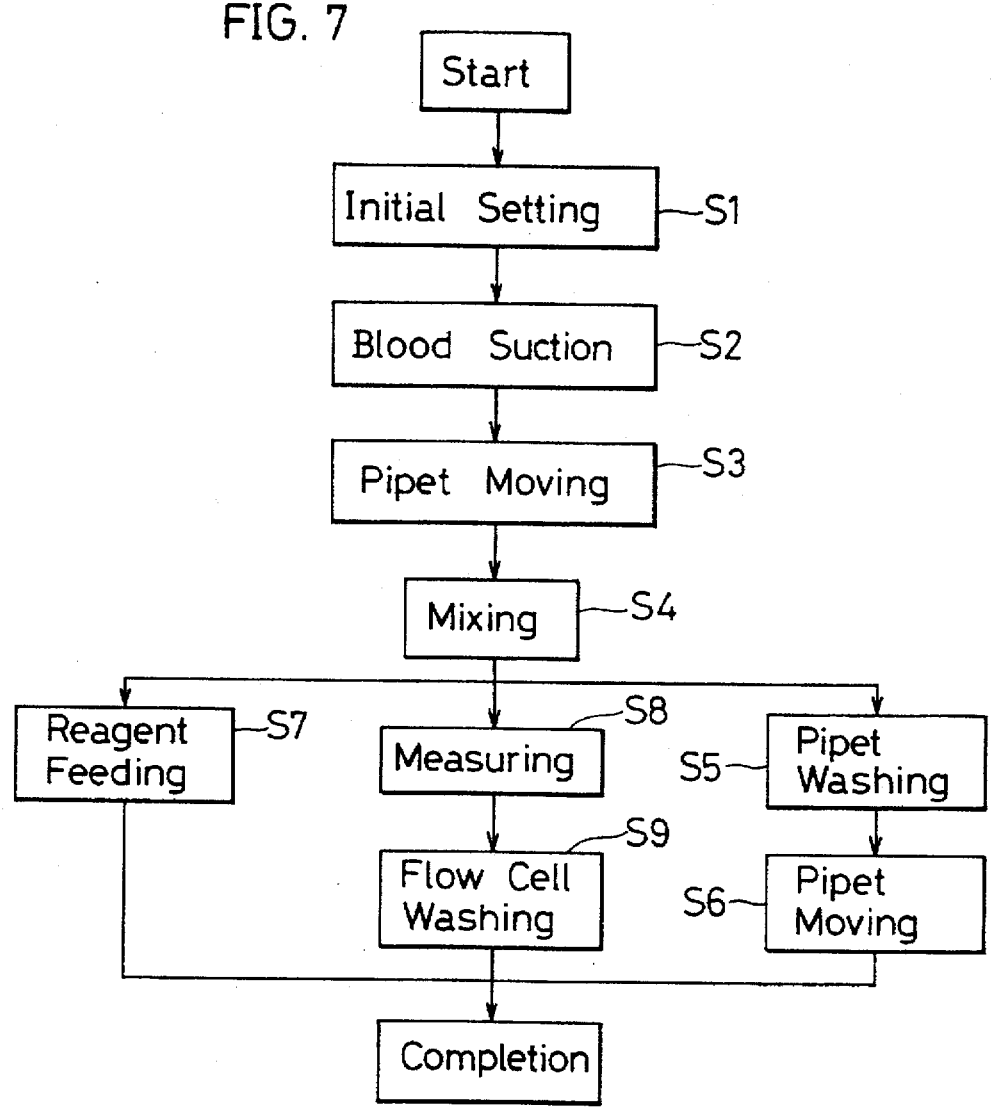
FIG. 7 is a flow chart illustrating a control section of a particle measuring apparatus according to the present invention.

Referring to a schematic flow chart shown in FIG. 7, operations of the particle measuring apparatus 10 will be described hereafter. Step S1 is an initial setting, at which time the dilution and count time are input by means of the keyboard. All the valves are closed.

Step S2 is a suction of blood as a specimen. When an unillustrated starting switch is activate, a necessary amount of the specimen is fed into the pipet 11 by the suction drive of the syringe S1. In addition, blood attached to the external wall of the pipet 11 is preferably wiped off.

Step S3 is a movement of the pipet 11. By driving the pipet moving mechanism, the pipet 11 is moved to a position above the mixing section 3 and then lowered. As soon as the mixing section 3 is closed by the seal member 16 which is connecting the periphery of the opening thereof, the drive of the pipet moving mechanism stops.

Step S4 is a mixing of the blood specimen, the reagents 1 and 2 in the mixing section 3. First, the blood specimen, the reagent 1 (buffer) and the reagent 2 (auramin O) are discharged into the mixing section 3 by opening the valves V5, V8, V9, V10 and V20 and driving the syringes S1, S4 and S5 for discharging. At the same time as the discharge starts, the valves V6 and V12 are opened, which allows the sheath liquid flow from the sheath chamber 71 into the waste liquid chamber 81 via the flow cell 4. Thus the inside of the flow cell 4 is cleaned. The flow rate of the blood specimen is 2.5 µl/sec, that of the reagent 2 is 10 µl/sec, that of the reagent 1 is 487.5 µl/sec, and all are discharged for four seconds. The dilution is 200 times [(2.5+10+487.5)/2.5]. The discharged amount of the blood specimen is 10 µl, that of the reagent 2 is 40 µl and that of the reagent 1 is 1,950 µl. The diluted specimen is fed into the pipeline indicated by a alternate long and short dash line between the mixing section 3 and the waste liquid chamber 81 in FIG. 1. At this moment the diluted specimen has not reached the flow cell 4 yet.

Step S5 is a cleaning of the pipet. By closing the valves V6, V12 and V20 first and opening the valves V4 and V13 for a certain time, for example four seconds, the sheath liquid is discharged from the pipet 11, and then collected in the waste liquid chamber 81 via the valve V4. At the same time, by opening the valve V7, the sheath liquid is also supplied into the inside of the mixing section 3 and collected in the waste liquid chamber 81 via the valve V4, cleaning the inside of the mixing section 3. Closing the valves V4, V7 V13 completes the cleaning.

Step S6 is a movement of the pipet 11. The pipet moving mechanism first raises the pipet 11 connecting the mixing section 3 and then moves the pipet 11 to the initial position above the rack.

Step S7 is a feeding of the reagents into the syringes S4 and S5, by closing the valves V8 and V9, opening the valves V16 and V17 and driving the syringes S4 and S5 for a necessary time for suction.

Step S8 is a measurement. First, the valves V6 and V12 are opened and at the same time the syringe S3 is driven for a necessary time for discharge, which makes the sheath liquid flow into the flow cell 4, thus a sheath flow formed in the pipe 43. After the sheath flow becomes stable, the measurement of particles is started. The results are displayed on the CRT 54.

Step S9 is a cleaning of the flow cell 4 and the part indicated by a alternate long and short dash line in FIG. 1. After the syringe S3 has stopped, the sheath liquid is kept flowing in the flow cell 4 for a while, which completes the cleaning of the flow cell 4. Then the nozzle is cleaned by closing the valve V6 and opening the valve V5. The cleaning of the nozzle is finished by closing the valve V12. For cleaning the pipe 43, the valve V5 is closed and at the same time the valves V4 and V20 are opened. The sheath liquid pressed in the sheath liquid chamber flows therefrom, via the valves V20 and V4, cleaning the passageways. Then the valve V5 is opened and the valves V4 and V20 are closed. By repeating the above operation three times, the diluted specimen remaining in the mixing section 3 and the waste liquid chamber 81 is washed away. Finally, after a sufficient amount of the sheath liquid is admitted in the line by closing the valve V5 and opening the valves V4 and V20, all the valves are closed to regain the initial state, the measurement being completed.

As in the above described embodiment of the invention, since the pipet 11, in the specimen discharge position, keeps the mixing section sealed, the specimen liquid and the reagent in the mixing section 3 can be transferred by pressure to the measuring section 5 by discharging the specimen from the specimen pipetting section 1 and the reagents from the reagent supply section 2. Therefore even though the amount of the specimen pipetted by the specimen pipetting section 1 is very small, the specimen can be pushed to the measuring section by the reagents discharged by the reagent supply section 2. That is, little specimen liquid remains in the passageways and the saving of the specimen can be realized.

Further it is possible to separately clean the passageways in the side of the reagent supply section 2 and those in the side of the particle measuring section 5 with the mixing section 3 as a boundary.

Further, only by controlling the driving rate for the syringes S4, S5 and S6 of the reagent supply section 2, the dilution of the specimen with the reagents can be easily changed in a wide range.

Further since it is possible to reduce the size of the mixing section 3, the saving of the washings for cleaning the inside of the mixing section is achieved, a small amount of the washings being sufficient for a complete cleaning.

Further since the seal member 16 is provided which is capable of keeping sealed up the mixing section 3 when the pipet 11 is in the specimen discharge position, the specimen or reagent does not leak out of the mixing section 3 when the reagents are discharged from the reagent supply section 2. Also, since the sealed mixing section 3 keeps the air outside from flowing thereinto, the liquid in the mixing section 3 is free of degeneration.

Figure 8:
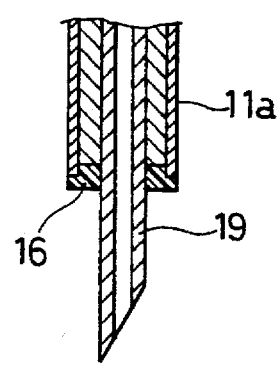
FIG. 8 is a cross sectional view of a tip of a pipet of another embodiment of the present invention.

The rod-like member 39 extending in the second passageway, provided as a turbulence generator in the mixing section 3, enables a homogeneous mixture of the specimen with the reagents. Other embodiments than described above are as follows: (a) Instead of the flat tip of the small diameter pipe 15 of the pipet in the above embodiment, the tip thereof may be formed in a sharp shape by cutting the tip diagonally as shown in FIG. 8. In this case, a bottom end 19 of the pipet can penetrate a cap into a specimen container capped thereby.

Figure 9:
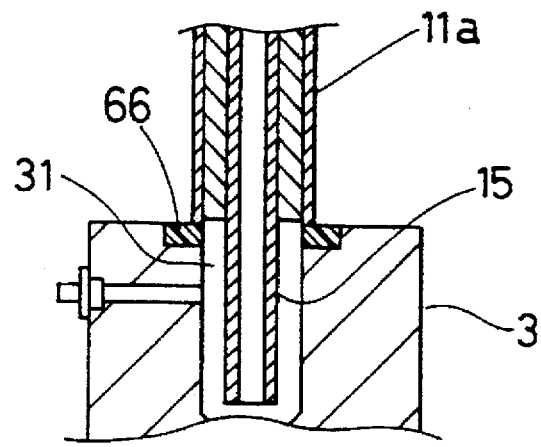
FIG. 9 is a cross sectional view of a seal mechanism of another embodiment of the present invention.

(b) Instead of the seal member 16 provided to the bottom part of the large diameter pipe 11a of the pipet to form a seal mechanism with the periphery of the opening of the cavity 31 in the above embodiment, the seal mechanism may be achieved by attaching a thin seal member 66 to the periphery of the opening of the cavity 31 to form a sealing with the bottom end of the large diameter pipe 11a of the pipet, as shown in FIG. 9. This can reduce a contact area of the specimen with the seal member.

Figure 10:
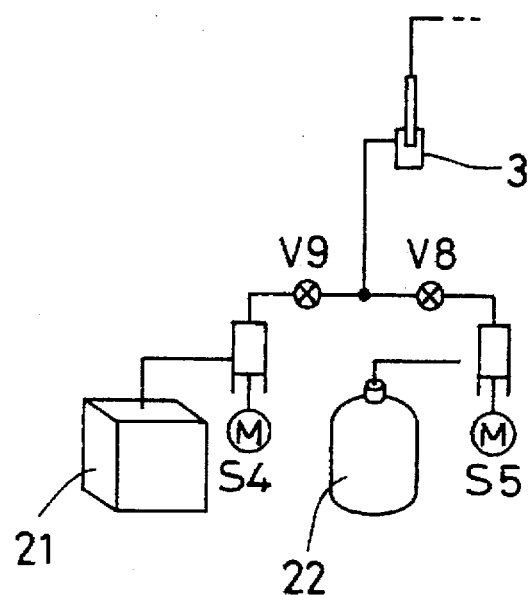
FIG. 10 is a diagram illustrating a piping of a reagent dispensing section of another embodiment of the present invention.

(c) Instead of the three reagent containers 21 to 23 disposed in the reagent supply section 2 which are connected to the mixing section 3 in the above embodiment, two reagent containers 21 and 22 may be disposed and connected to the mixing section 3, as shown in FIG. 10. In this case, the passageways connecting all the reagent containers with the mixing section 3 can be integrated to one line system. This is effective when the reagents remaining in the passageways do not react each other, namely do not decompose or degenerate, with any influence on a following discharge of the reagents.

Figure 11:
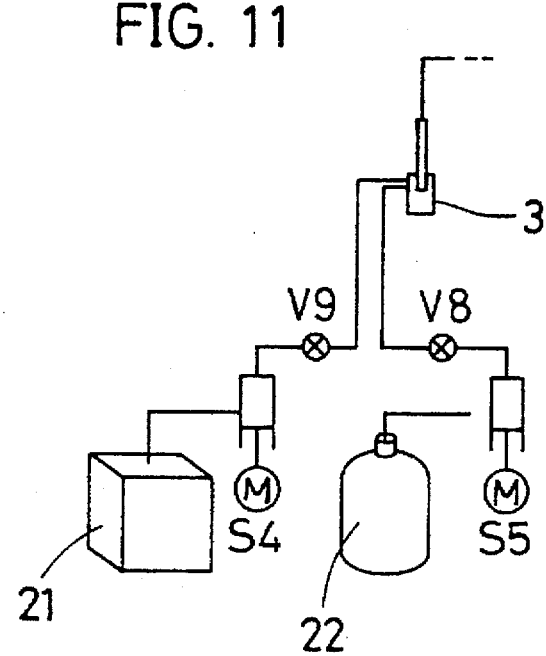
FIG. 11 is a diagram illustrating a piping of a reagent dispensing section of still another embodiment of the present invention.
Figure 12:
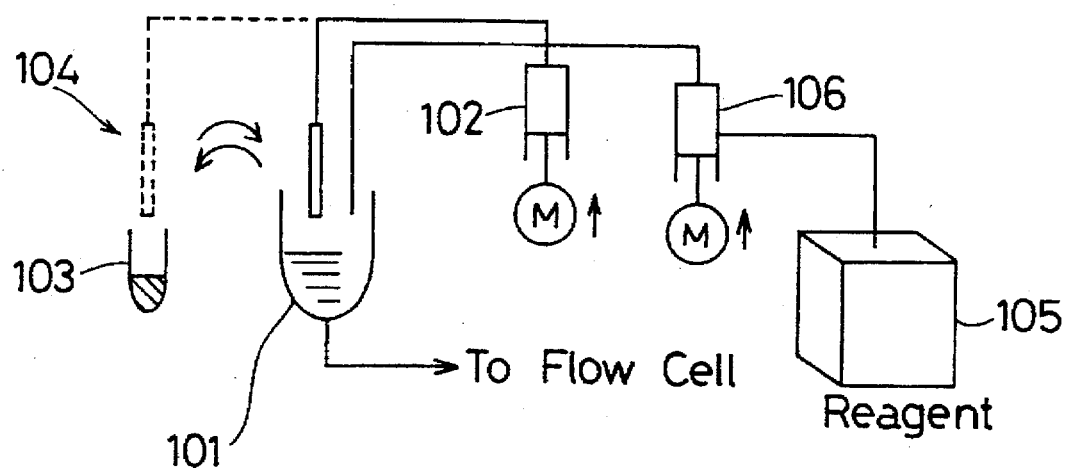
FIG. 12 illustrates a conventional method of dispensing a specimen using an open chamber.
Figure 13:
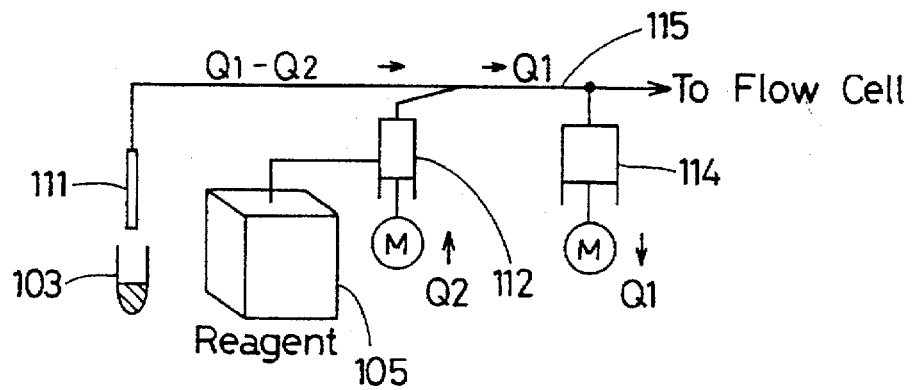
FIG. 13 illustrates a conventional method of dispensing a specimen using a difference of flow rates.
Figure 14:
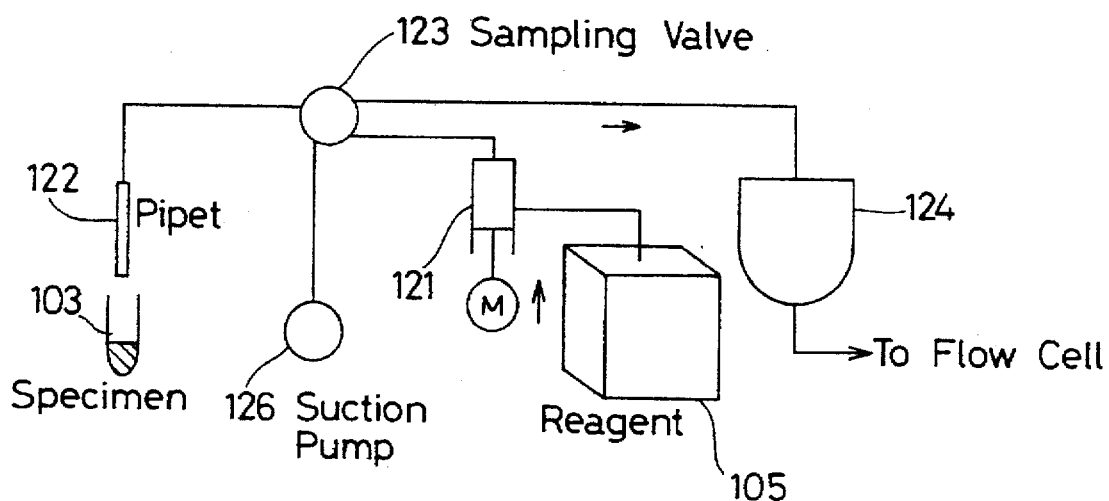
FIG. 14 illustrates a conventional method of dispensing a specimen using a sampling valve.

Alternatively the two reagent containers 21 and 22 may be constructed as shown in FIG. 11 in such a manner that the reagent containers separately send the reagents to the mixing section 3 by the respective passageways, not by the joint passage in the embodiment just described. This is effective for the reagents which react each other.

In the invention wherein the specimen pipetting section is so constructed as to be positioned in the first state of picking up the specimen liquid as well as in the second state of supplying the specimen liquid into the mixing section, the mixing section is open when the specimen pipetting section is in the first state, and the mixing section is kept closed by the specimen pipetting section in the second state, so that the reagent dispensed by the reagent dispenser presses and transfers the specimen liquid in the mixing section out toward the particle measuring section; a small mixing section is enough for mixing the specimen liquid and the reagent whatever amount of the specimen liquid is used, and also the specimen pipetting section meets various requirements in the amount of the specimen liquid used because the specimen pipetting section can repeatedly move between the first state and the second state to supply a necessary amount of the specimen liquid placed in the specimen pipetting position. Thus the mixing section can be downsized.

Besides no additional means for transferring the specimen liquid toward the particle measuring section is required, which makes the structure of the apparatus simple. And since the specimen pipetted by the specimen pipetting section can be transferred to the measuring section together with the reagent discharged by the reagent dispensing means, the amount of the specimen can be reduced.

Further only by controlling the discharge rate of the reagent dispensers, a desired dilution of the specimen with the reagents can be selected from a wide range of dilutions. That can meet various requirements in the dilution of the specimen.

Further the reduction in the size of the mixing section can save the amount of the washings for cleaning the inside thereof, only a little amount being sufficient for the cleaning. Also the cleaning can be completed in shorter time.

When the particle measuring apparatus has such a construction that the specimen pipetting means contains the tube-like pipet, the mixing section comprises the container with the opening for receiving the specimen liquid, and the mixing section is kept closed by contacting the periphery of the pipet with the opening, the pressure produced by the reagent discharged into the mixing section does not escape from the mixing part kept well-closed, thus the specimen liquid being exactly transferred into the particle measuring section. Moreover the mixing section shut off from the air can prevent the degeneration of the liquids mixed therein, thus the accuracy of the measurement improved.

When the turbulence generating device is provided in the mixing section or in the passageway communicating the mixing section with the particle measuring section, the generated turbulent flow can mix more homogeneously the specimen and reagent liquids therein, therefore a more accurate measurement obtained.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A particle measuring apparatus comprising:

specimen pipetting means for pipetting specimen liquid;

reagent dispensing means for dispensing a reagent;

a mixing section for receiving the specimen liquid supplied by the specimen pipetting means and the reagent dispensed by the reagent dispensing means;

a particle measuring section for receiving the specimen liquid and the reagent transferred from the mixing section and measuring particles in the specimen liquid diluted by the reagent;

wherein the specimen pipetting means is so constructed as to be positioned in a first state of picking up the specimen liquid as well as in a second state of supplying the specimen liquid into the mixing section, the mixing section is open when the specimen pipetting means is in the first state, and the mixing section is kept closed by the specimen pipetting means in the second state so that the reagent dispensed by the reagent dispensing means presses and transfer the specimen liquid in the mixing section out toward the particle measuring section; and setting means for variably setting at least one of a dilution of the specimen liquid with the reagent and a specimen count time for counting particles in the diluted specimen liquid.

2. A particle measuring apparatus according to claim 1 wherein the specimen pipetting means comprises a tube-like pipet, the mixing section comprises a container with an opening for receiving the specimen liquid, and the mixing section is kept closed by contacting the periphery of the pipet with the opening.

3. A particle measuring apparatus according to claim 2 wherein the periphery of the pipet and the opening of the container contact each other with a seal member therebetween.

4. A particle measuring apparatus according to claim 1 wherein, in the mixing section or in a passageway communicating the mixing section with the particle measuring section, a turbulence generating means is provided for generating a turbulent flow in the specimen liquid and reagent transferred therein.

5. A particle measuring apparatus according to claim 4 wherein the turbulence generating means comprises a member projecting into the mixing section or into the passageway communicating the mixing section with the particle measuring section.

6. A particle measuring apparatus according to claim 5 wherein the mixing section is provided with a passageway for accepting washings, the passageway communicating the mixing section with the particle measuring section is provided with a branch passageway for discharging a waste liquid, and the projecting member is a rod-like member inserted through the branch passageway whose tip projects into the communicating passageway.

7. A particle measuring apparatus according to claim 1 comprising a plurality of reagent dispensing means provided with their respective passageways which join together to communicate with the mixing section.

8. A particle measuring apparatus according to claim 1 comprising a plurality of reagent dispensing means each of which is provided with a passageway independently communicating with the mixing section.

9. A particle measuring apparatus according to claim 1, wherein said specimen pipetting means includes a pipet having a sharp shape at its bottom end, said bottom end thereby being capable of penetrating a cover on a specimen container containing said specimen liquid.

10. A particle measuring apparatus according to claim 1, wherein said setting means includes a display facilitating selection of at least one of said dilution and said specimen count time.

11. A particle measuring apparatus according to claim 1, further comprising determining means for determining an amount of specimen liquid, an amount of the reagent, and a suction amount required by said specimen pipetting means in accordance with said dilution set by said setting means.

12. A particle measuring apparatus according to claim 1, further comprising determining means for determining an analyzed amount, an amount of specimen at a predetermined dilution, and a total required time for measurement in accordance with said specimen count time set by said setting means.

13. A particle measuring apparatus according to claim 1, further comprising a control valve disposed between the mixing section and the particle measuring section for controlling communication of the diluted specimen liquid from the mixing section to the particle measuring section, the mixing section having an inner volume suitable for mixing the specimen liquid with the reagent, wherein cooperation of the control valve and the reagent dispensing means allows the hold-up time of the diluted specimen liquid in the mixing section to be adjusted, so that the diluted specimen liquid suitable for the measuring of particles can be introduced.

14. A particle measuring apparatus comprising:

specimen pipetting means for pipetting specimen liquid;

reagent dispensing means for dispensing a reagent;

a mixing section for receiving the specimen liquid supplied by the specimen pipetting means and the reagent dispensed by the reagent dispensing means;

a particle measuring section for receiving the specimen liquid and the reagent transferred from the mixing section and measuring particles therein;

wherein the specimen pipetting means is so constructed as to be positioned in a first state of picking up the specimen liquid as well as in a second state of supplying the specimen liquid into the mixing section, the mixing section is open when the specimen pipetting means is in the first state, and the mixing section is kept closed by the specimen pipetting means in the second state so that the reagent dispensed by the reagent dispensing means presses and transfer the specimen liquid in the mixing section out toward the particle measuring section;

a passageway for accepting washings provided in the mixing section;

a branch passageway, provided in said passageway communicating the mixing section with the particle measuring section, for discharging a waste liquid; and a turbulence generating means for generating a turbulent flow inserted through the branch passageway whose tip projects into the communicating passageway.

15. A method for measuring particles comprising the steps of:

pipetting specimen liquid by a specimen pipetting unit;

dispensing a reagent;

mixing the specimen liquid supplied by said pipetting step and the reagent dispensed by said reagent dispensing in a mixing section;

measuring particles supplied by said mixing step;

positioning said specimen pipetting unit in a first state of picking up the specimen liquid and in a second state of supplying the specimen liquid into the mixing section, the mixing section being open when the specimen pipetting unit is in the first state, and the mixing section being closed by the specimen pipetting unit in the second state, thereby pressing and transferring the specimen liquid from said mixing step to said particle measuring step, via the reagent dispensed by the reagent dispensing step presses; and variably setting at least one of a dilution of the specimen liquid with the reagent and a specimen count time.

16. A method according to claim 15, wherein said setting step includes displaying selection of at least one of said dilution and said specimen count time.

17. A method according to claim 15, further comprising determining an amount of specimen liquid, an amount of the reagent, and a suction amount required by said specimen pipetting unit in accordance with said dilution set by said setting step.

18. A particle measuring method according to claim 15, further comprising determining an analyzed amount, an amount of specimen at a predetermined dilution, and a total required time for measurement in accordance with said specimen count time set by said setting step.

19. A method according to claim 15, further comprising:

providing a passageway for accepting washings in the mixing section;

providing a branch passageway in a passageway communicating the mixing section with a particle measuring section, for discharging a waste liquid; and generating a turbulent flow through the branch passageway into the communicating passageway.

20. A method according to claim 15, further comprising controlling communication of the diluted specimen liquid from the mixing section to the particle measuring section, wherein cooperation of the controlling step and the reagent dispensing step allows adjusting of the hold-up time of the diluted specimen liquid in the mixing section, so that the diluted specimen liquid suitable for the measuring of particles can be introduced.

* * * * *